United States Patent
Arai (10) Patent No.: US 11,832,795 B2
(45) Date of Patent: Dec. 5, 2023

(54) FLUID CONTROL DEVICE FOR ENDOSCOPE, AND ENDOSCOPE

(71) Applicant: OLYMPUS CORPORATION, Tokyo (JP)

(72) Inventor: Norimasa Arai, Chofu (JP)

(73) Assignee: OLYMPUS CORPORATION, Tokyo (JP)

( * ) Notice: Subject to any disclaimer, the term of this patent is extended or adjusted under 35 U.S.C. 154(b) by 547 days.

(21) Appl. No.: 17/065,830

(22) Filed: Oct. 8, 2020

(65) Prior Publication Data

US 2021/0076914 A1 Mar. 18, 2021

Related U.S. Application Data

(63) Continuation of application No. PCT/JP2019/005398, filed on Feb. 14, 2019.

(30) Foreign Application Priority Data

Apr. 16, 2018 (JP) .................................. 2018-078683

(51) Int. Cl.
*A61B 1/00* (2006.01)
*A61B 1/015* (2006.01)

(52) U.S. Cl.
CPC .......... *A61B 1/015* (2013.01); *A61B 1/00006* (2013.01); *A61B 1/00119* (2013.01); *A61B 1/00068* (2013.01)

(58) Field of Classification Search
CPC . A61B 1/015; A61B 1/00006; A61B 1/00119; A61B 1/00068; A61B 1/00; B02B 23/24; A61M 13/003

USPC ..................................... 600/156, 158, 159
See application file for complete search history.

(56) References Cited

U.S. PATENT DOCUMENTS

| | | | | |
|---|---|---|---|---|
| 5,692,729 A | * | 12/1997 | Harhen | ............. A61B 1/015 251/9 |
| 2013/0303844 A1 | * | 11/2013 | Grudo | ........... A61B 1/00064 600/101 |
| 2015/0305599 A1 | | 10/2015 | Murayama | |
| 2016/0262600 A1 | | 9/2016 | Yamaoka | |

FOREIGN PATENT DOCUMENTS

| | | |
|---|---|---|
| EP | 3066973 A1 | 9/2016 |
| JP | 2005-177208 A | 7/2005 |
| JP | 2014-117338 A | 6/2014 |
| JP | 5722510 B1 | 5/2015 |
| JP | 2018-148963 A | 9/2018 |
| WO | WO 2015/098229 A1 | 7/2015 |

OTHER PUBLICATIONS

International Search Report dated Apr. 16, 2019 issued in PCT/JP2019/005398.

* cited by examiner

*Primary Examiner* — Timothy J Neal
*Assistant Examiner* — James Edward Boice
(74) *Attorney, Agent, or Firm* — Scully, Scott, Murphy & Presser, P.C.

(57) ABSTRACT

A fluid control device for endoscope includes a gas feeding conduit, an operation button and a deforming portion. The deforming portion is disposed on a downstream side with respect to the operation button, and has a closing portion which is brought into contact with an inner wall of the gas feeding conduit in a state where the operation button is not pushed.

20 Claims, 5 Drawing Sheets

FLUID CONTROL DEVICE FOR ENDOSCOPE, AND ENDOSCOPE

CROSS REFERENCE TO RELATED APPLICATION

This application is a continuation application of PCT/JP2019/005398 filed on Feb. 14, 2019 and claims benefit of Japanese Application No. 2018-078683 filed in Japan on Apr. 16, 2018, the entire contents of which are incorporated herein by this reference.

BACKGROUND OF THE INVENTION

1. Field of the Invention

The present invention relates to a fluid control device for endoscope and an endoscope which include a gas feeding conduit having a flow passage through which a gas flows from an upstream side to a downstream side.

2. Description of the Related Art

Recently, an endoscope has been popularly used in a medical field. The endoscope used in the medical field can observe an organ in a body cavity by inserting an elongated insertion section into the body cavity which is a subject. When necessary, various treatments can be performed using a treatment instrument inserted into an insertion channel for treatment instrument which the endoscope includes.

An endoscope having a following configuration is well known. In the endoscope, besides the above-mentioned insertion channel, a front side water feeding conduit which supplies a liquid into the subject, and a gas/water feeding conduit which feeds a liquid or a gas to an objective lens mounted on a distal end surface of the insertion section and the like are disposed.

A configuration of an endoscope is also well known where an insertion channel is used as a suction conduit for suctioning a fluid such as a liquid (for example, a body liquid) or a gas in the subject.

Further, a configuration of an endoscope is also well known where, to realize thinning of a diameter of the insertion section, only one conduit is disposed in the endoscope, and gas is fed to a subject or a fluid in the subject is suctioned using the one endoscope conduit.

As an endoscope which includes an insertion section having an extremely small diameter, for example, an endoscope used in the field of otolaryngology is well known.

More specifically, a configuration of an endoscope is well known where one endoscope conduit is disposed in an insertion section and an operation section continuously connected to a proximal end of the insertion section, a fluid control device for endoscope (hereinafter, simply referred to as fluid control device) which switches between feeding of a gas into a subject and suction of a fluid in the subject using the one endoscope conduit and to which a gas feeding conduit and a suction conduit are connected is disposed in the operation section.

The gas feeding conduit and the suction conduit each communicate with the endoscope conduit in the fluid control device, and the gas feeding conduit is connected to a gas feeding device, and the suction conduit is connected to a suction device.

Further, a configuration of a fluid control device is also well known where a valve element which opens a flow passage of a gas feeding conduit only with the supply of a gas from an upstream side to a downstream side in the gas feeding conduit, and prevents the backward flow of a liquid toward an upstream side of the flow passage is disposed in the gas feeding conduit.

Japanese Patent No. 5722510 discloses a configuration of a fluid control device where a suction button which performs a suction instruction is disposed on an upstream side with respect to the above-mentioned valve element in the gas feeding conduit, and the suction button itself functions as another valve element different from the above-mentioned valve element.

SUMMARY OF THE INVENTION

According to an aspect of the present invention, there is provided a fluid control device for endoscope which includes: a gas feeding conduit having a flow passage through which a gas flows from an upstream side to a downstream side, the gas feeding conduit having a side hole which causes the flow passage and an external space to communicate with each other in an intermediate portion of the gas feeding conduit; an operation button inserted into the side hole and disposed to be operable by pushing in a penetrating direction of the side hole; and a deforming portion continuously connected with the operation button and disposed in the gas feeding conduit, the deforming portion configured to be brought into contact with an inside of the gas feeding conduit thus closing the flow passage in a state where the operation button is not pushed, and the deforming portion configured to be deformed in the penetrating direction thus opening the flow passage in a state where the operation button is pushed, wherein the deforming portion is disposed on a downstream side with respect to the operation button, and has a closing portion which is brought into contact with an inner wall of the gas feeding conduit in the state where the operation button is not pushed.

According to another aspect of the present invention, there is provided an endoscope which includes: an insertion section in which a fluid conduit is disposed; an operation section continuously connected to the insertion section; and a fluid control device mounted on the operation section and having a conduit opening configured to communicate with the fluid conduit disposed in the insertion section, wherein the fluid control device includes: a connecting portion disposed at a position different from the conduit opening and connected to a fluid source; a gas feeding conduit having a flow passage through which a gas flows from an upstream side which is a side of the fluid source to a downstream side which is a side of the conduit opening, the gas feeding conduit having a side hole which causes the flow passage and an external space to communicate with each other in an intermediate portion of the gas feeding conduit; an operation button inserted into the side hole and disposed to be operable by pushing in a penetrating direction of the side hole; and a deforming portion continuously connected with the operation button and disposed in the gas feeding conduit, the deforming portion configured to be brought into contact with an inside of the gas feeding conduit thus closing the flow passage in a state where the operation button is not pushed, and the deforming portion configured to be deformed in the penetrating direction thus opening the flow passage in a state where the operation button is pushed, wherein the deforming portion is disposed on a downstream side with respect to the operation button, and has a closing portion which is brought into contact with an inner wall of the gas feeding conduit in the state where the operation button is not pushed.

DETAILED DESCRIPTION OF THE PREFERRED EMBODIMENT

Hereinafter, an embodiment of the present invention is described with reference to drawings. Drawings are schematic views. Accordingly, it must be noted that a relationship between a thickness and a width of each member, a ratio between thicknesses of respective members and the like differ from the corresponding relationships of members of an actual fluid control device for endoscope. Needless to say, portions of the fluid control device are described with different size relationship or different ratios between the drawings.

Figure 1:
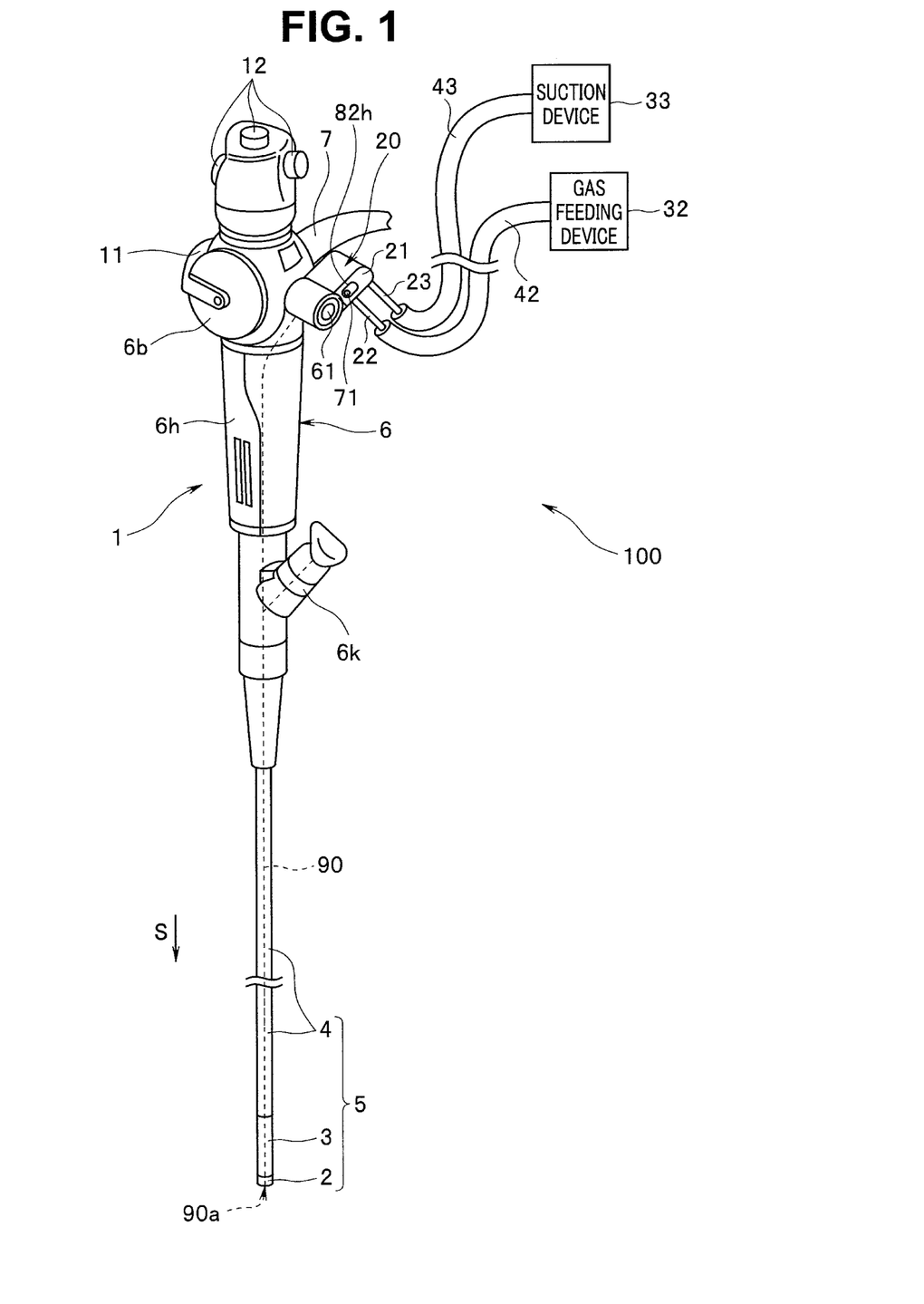
FIG. 1 is a view of an endoscope apparatus schematically showing an external appearance of an endoscope provided with a fluid control device according to an embodiment together with a gas feeding device and a suction device.

FIG. 1 is a view of an endoscope apparatus schematically showing an external appearance of an endoscope provided with a fluid control device according to the embodiment together with a gas feeding device and a suction device.

As shown in FIG. 1, an endoscope apparatus 100 is mainly constituted of an endoscope 1, a gas feeding/suction valve 20 which is a fluid control device, a gas feeding device 32, a suction device 33, a gas feeding tube 42 and a suction tube 43.

The endoscope 1 includes: an insertion section 5 inserted into a subject; and an operation section 6 continuously connected to a proximal end side of the insertion section 5 in an insertion direction S.

The endoscope 1 includes: a universal cord 7 extending from the operation section 6; and a connector not shown mounted on an extending end of the universal cord 7. The endoscope 1 is electrically connected to external devices such as a control device and an illumination device through the connector.

The insertion section 5 is constituted of a distal end portion 2, a bending portion 3 and a flexible tube portion 4 in order from a distal end side in the insertion direction S. The insertion section 5 is formed in an elongated shape in the insertion direction S.

The bending portion 3 is bent in, for example, two directions, by a rotary operation of a bending lever 11 described later. By bending the bending portion 3, it is possible to change an observation direction of an objective optical system not shown disposed in the distal end portion 2, and it is possible to enhance insertability of the distal end portion 2 in the subject. The bending portion 3 may be bent in three or more directions. The flexible tube portion 4 is continuously connected to a proximal end side of the bending portion 3.

A grasping portion 6h grasped by an operator is mounted on the operation section 6. A pipe sleeve 6k which is a liquid feeding port is mounted on the operation section 6 on the distal end side in the insertion direction S with respect to the grasping portion 6h.

The pipe sleeve 6k is mounted on the operation section 6 on a downstream side with respect to a connecting portion G (see FIG. 4) described later, and communicates with a flow passage 90i of an endoscope conduit 90 described later (both shown in FIG. 4) on a downstream side with respect to the connecting portion G.

The pipe sleeve 6k has an insertion/removal opening 90c which communicates with the flow passage 90i for inserting or removing a treatment instrument into or from a subject through the flow passage 90i.

The insertion/removal opening 90c constitutes a mounting opening on which a syringe 120 (see FIG. 4) is mounted at the time of feeding a liquid R (see FIG. 4) into the subject through the flow passage 90i.

On an operation section body 6b positioned on a proximal end side in the insertion direction S with respect to the grasping portion 6h of the operation section 6, the bending lever 11 which instructs bending of the bending portion 3 in two directions, and operation switches 12 which instructs an image pickup operation of an image pickup unit not shown mounted in the distal end portion 2 are disposed.

The gas feeding/suction valve 20 which switches between a supply of a gas A (see FIG. 6) into the subject and a suction of a fluid E (see FIG. 5) through the endoscope conduit 90 is mounted on the operation section body 6b.

The gas feeding device 32 is connected to a gas feeding pipe sleeve 22 described later of the gas feeding/suction valve 20 through the gas feeding tube 42, and the suction device 33 is connected to a suction pipe sleeve 23 described later of the gas feeding/suction valve 20 through the suction tube 43.

Hereinafter, a configuration of the gas feeding/suction valve 20 is described with reference to FIG. 1 described above and FIG. 2 to FIG. 6.

Figure 2:
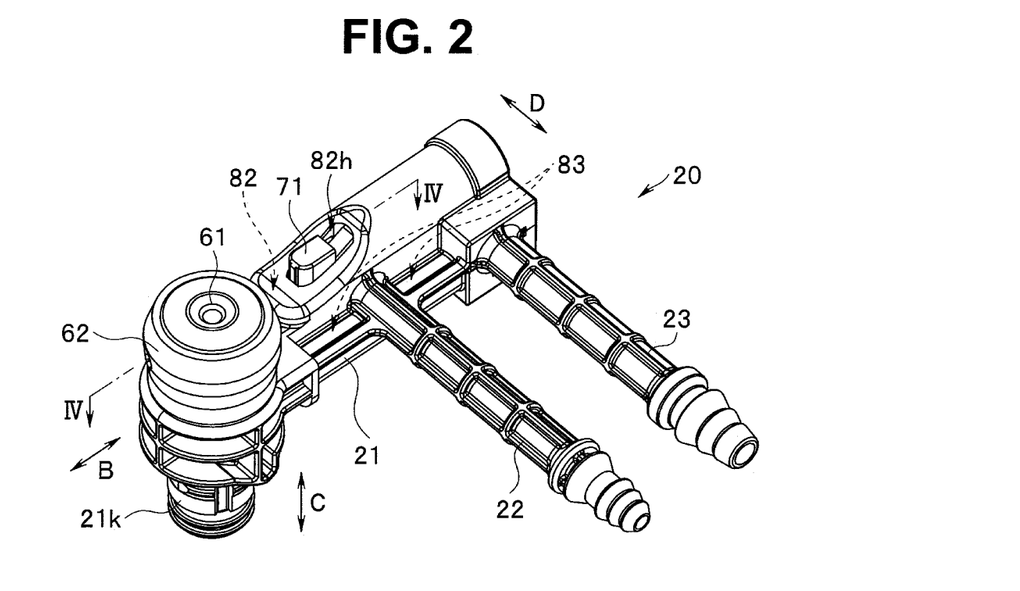
FIG. 2 is a perspective view of a fluid control device shown in FIG. 1.
Figure 3:
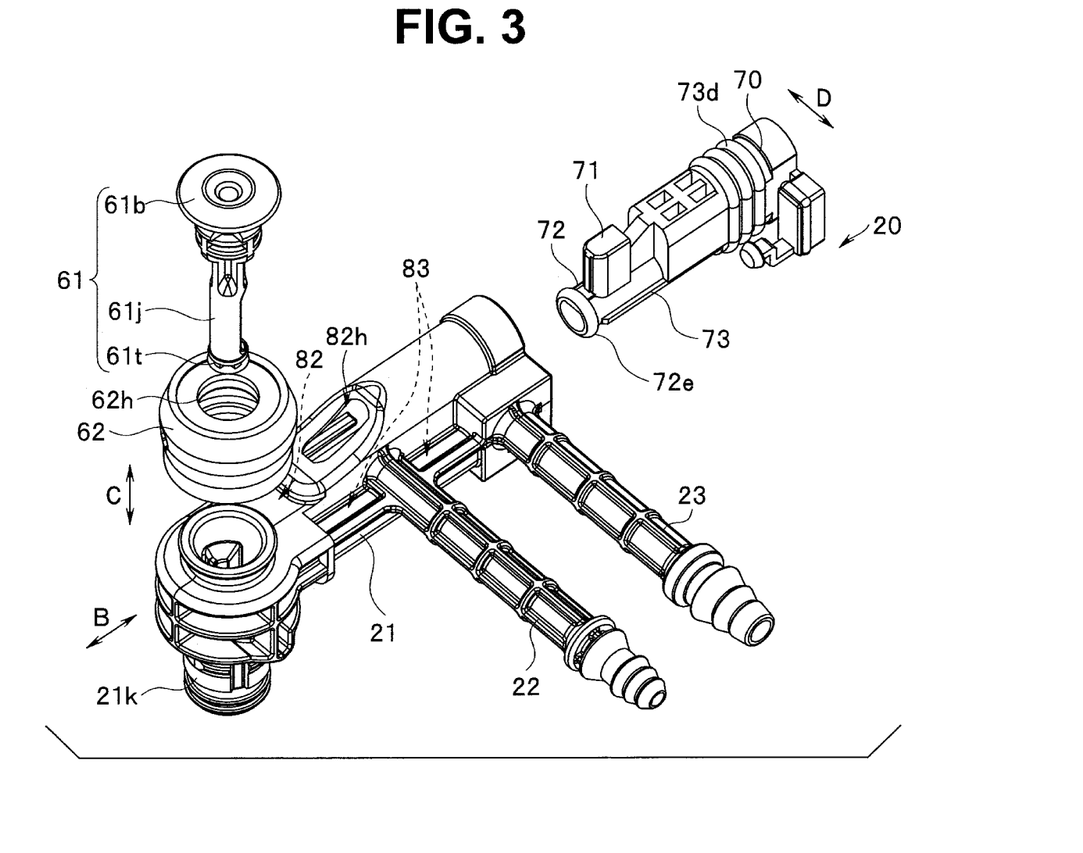
FIG. 3 is an exploded perspective view of the fluid control device shown in FIG. 2.
Figure 4:
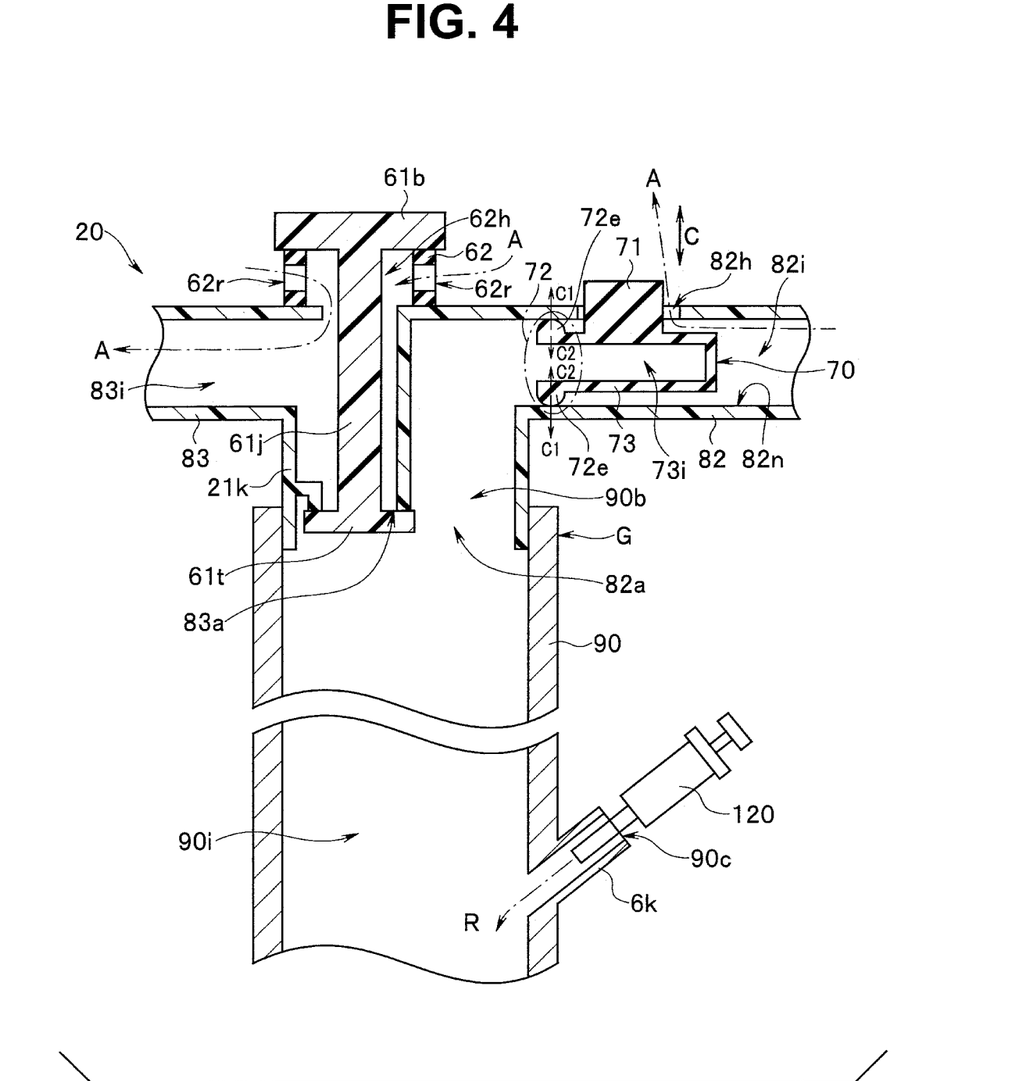
FIG. 4 is a cross-sectional view of the fluid control device shown in FIG. 2 taken along a line IV-IV in FIG. 2 together with an endoscope conduit and a syringe.

FIG. 2 is a perspective view of the fluid control device shown in FIG. 1. FIG. 3 is an exploded perspective view of the fluid control device shown in FIG. 2. FIG. 4 is a cross-sectional view of the fluid control device shown in FIG. 2 taken along a line IV-IV in FIG. 2 together with the endoscope conduit and the syringe.

Figure 5:
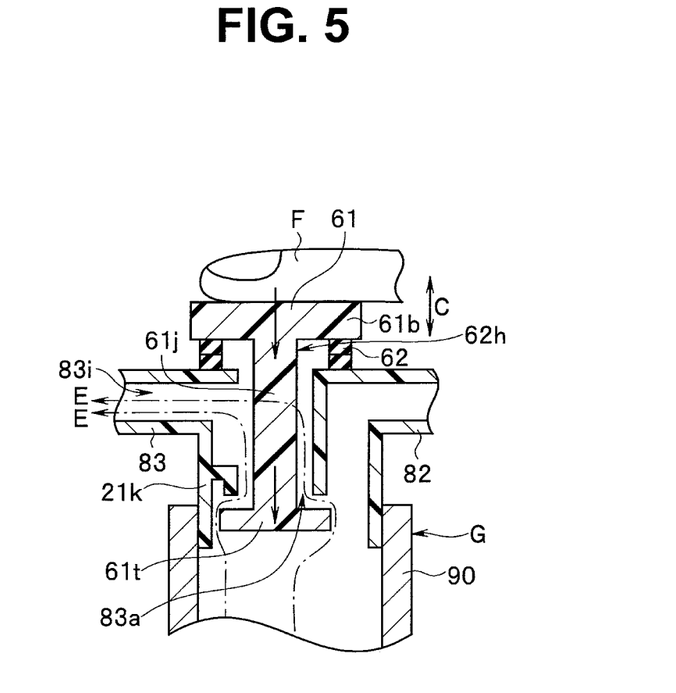
FIG. 5 is a partial cross-sectional view showing a state where a suction button unit shown in FIG. 4 is operated by an operator by pushing.
Figure 6:
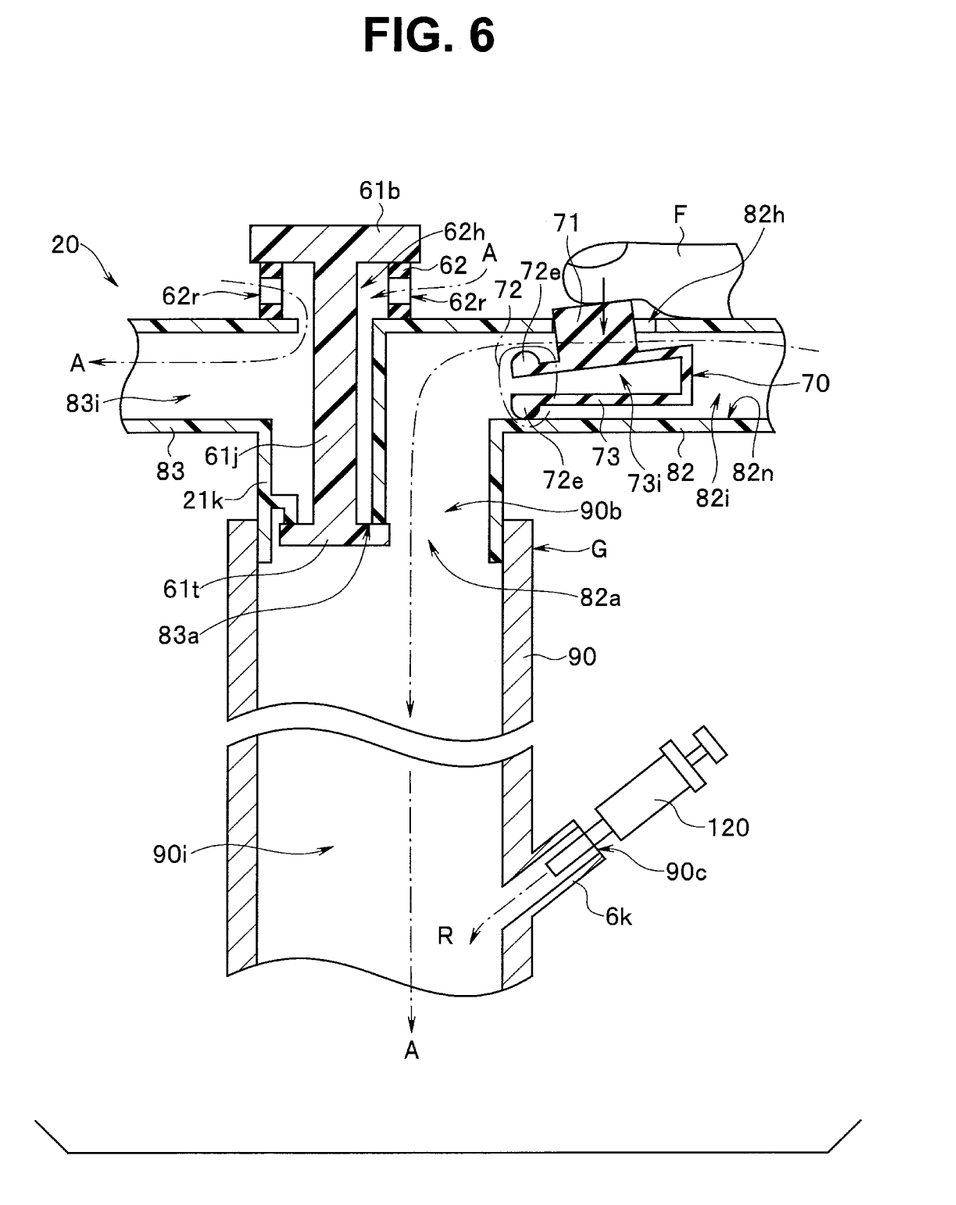
FIG. 6 is a cross-sectional view showing a state where a gas feeding button shown in FIG. 4 is operated by the operator by pushing.

FIG. 5 is a partial cross-sectional view showing a state where a suction button unit shown in FIG. 4 is operated by an operator by pushing. FIG. 6 is a cross-sectional view showing a state where a gas feeding button shown in FIG. 4 is operated by the operator by pushing.

Regarding cross sections of the gas feeding/suction valve 20 shown in FIG. 4 to FIG. 6, an advancing direction of the suction conduit 83 is intentionally described in an opposite direction with respect to the cross sections at a position taken along the line IV-IV in FIG. 2 in order to facilitate an understanding of a configuration for connecting a suction conduit 83 to the endoscope conduit 90.

As shown in FIG. 1, one endoscope conduit 90 is formed in the insertion section 5 and the operation section 6.

A distal end of the flow passage 90i of the endoscope conduit 90 in the insertion direction S opens as an opening 90a at a distal end surface of the distal end portion 2 as shown in FIG. 1.

As shown in FIG. 4, a proximal end of the flow passage 90*i* opens as an opening 90*b* in the gas feeding/suction valve 20. As shown in FIG. 4, the pipe sleeve 6*k* communicates with the flow passage 90*i* at an intermediate position of the flow passage 90*i* in the operation section 6.

As shown in FIG. 2 to FIG. 4, the gas feeding/suction valve 20 mounted on the operation section body 6*b* of the operation section 6 of the endoscope 1 is mainly constituted of a gas feeding conduit 82, the suction conduit 83, the gas feeding pipe sleeve 22 which communicates with the gas feeding conduit 82, the suction pipe sleeve 23 which communicates with the suction conduit 83, the suction button unit 61, a rubber spring 62 having suction leak holes 62*r*, and a gas feeding button unit 70.

The gas feeding conduit 82 is disposed in the gas feeding/suction valve 20 in a direction B shown in FIG. 2 and FIG. 3, and has a flow passage 82*i* through which a gas A flows from an upstream side to a downstream side.

In an intermediate portion of the gas feeding conduit 82 in the direction B, as shown in FIG. 2 to FIG. 4, a side hole 82*h* which causes the flow passage 82*i* and an external space to communicate with each other is formed in a direction C orthogonal to the direction B in FIG. 2 to FIG. 4. Hereinafter, the direction C is referred to as a penetrating direction C.

The gas feeding conduit 82 communicates with the gas feeding pipe sleeve 22 on an upstream side (gas feeding device 32 side), and an opening end 82*a* of the gas feeding conduit 82 on a downstream side is connected to the opening 90*b* of the endoscope conduit 90 in the gas feeding/suction valve 20 at the connecting portion G such that the flow passage 82*i* communicates with the flow passage 90*i*.

With such a configuration, as shown in FIG. 6, in a state where a gas feeding button 71 described later is pushed, the gas A fed from the gas feeding device 32 enters the flow passage 82*i* of the gas feeding conduit 82 through the gas feeding tube 42 and the gas feeding pipe sleeve 22, then is supplied into a subject from the opening 90*a* through the flow passage 90*i* of the endoscope conduit 90.

As shown in FIG. 4, in a state where the gas feeding button 71 described later is not pushed, the gas A fed from the gas feeding device 32 flows out to the external space from the flow passage 82*i* through the side hole 82*h*. In other word, the side hole 82*h* constitutes a passage through which the gas A in the flow passage 82*i* flows out to the external space in a state where the gas feeding button 71 is not pushed.

The suction conduit 83 is disposed in the gas feeding/suction valve 20 in the direction B shown in FIG. 2 and FIG. 3, and is arranged parallel to the gas feeding conduit 82 in a direction D orthogonal to the penetrating direction C and the direction B. The suction conduit 83 has a flow passage 83*i* through which a fluid E flows from a downstream side to an upstream side.

The suction conduit 83 communicates with the suction pipe sleeve 23 on an upstream side (suction device 33 side), and an opening end 83*a* of the suction conduit 83 on a downstream side is connected to the opening 90*b* of the endoscope conduit 90 in the gas feeding/suction valve 20 at the connecting portion G such that the flow passage 83*i* communicates with the flow passage 90*i*.

As shown in FIG. 3, the suction button unit 61 is constituted of a shaft portion 61*j*, a pushing portion 61*b* and a sealing portion 61*t*.

The suction button unit 61 is configured to be operable by pushing in the penetrating direction C as shown in FIG. 4 and FIG. 5 by a finger F of an operator.

In other word, when the operator performs a pushing operation of the suction button unit 61 with his/her finger F in the penetrating direction C as shown in FIG. 5, the suction button unit 61 moves downward in the penetrating direction C in FIG. 5, that is, toward an endoscope conduit 90 side.

When the pushing operation is finished, the suction button unit 61 moves upward in the penetrating direction C in FIG. 4, that is, toward a side away from the endoscope conduit 90.

The shaft portion 61*j* is fitted in a fitting hole 21*k* of the gas feeding/suction valve 20 and a through hole 62*h* of the rubber spring 62 each formed in the penetrating direction C. The shaft portion 61*j* is formed in an elongated shape, for example, a circular columnar shape in the penetrating direction C in FIG. 3.

The pushing portion 61*b* is formed in a disc shape, for example. The pushing portion 61*b* is formed on an upper end of the shaft portion 61*j* in the penetrating direction C in FIG. 3, and is brought into contact with the rubber spring 62 in a state where the rubber spring 62 is sandwiched between the pushing portion 61*b* and an exterior of the gas feeding/suction valve 20 in the penetrating direction C.

The sealing portion 61*t* is formed on a lower end of the shaft portion 61*j* in the penetrating direction C in FIG. 3, and is fitted in the fitting hole 21*k* together with the shaft portion 61*j*. The sealing portion 61*t* is formed in a flange shape having a diameter larger than a diameter of the shaft portion 61*j*.

The sealing portion 61*t* closes the opening end 83*a* of the suction conduit 83 in a state where the suction button unit 61 is not pushed.

Accordingly, in a state where the suction button unit 61 is pushed, as shown in FIG. 5, the sealing portion 61*t* opens the opening end 83*a* thus causing the flow passage 83*i* and the flow passage 90*i* to communicate with each other.

As shown in FIG. 2 and FIG. 3, the through hole 62*h* is formed in the rubber spring 62 in the penetrating direction C. The rubber spring 62 has a predetermined length in the penetrating direction C and is formed in a cylindrical shape.

The rubber spring 62 is configured to be extendable and contractible in the penetrating direction C. As shown in FIG. 4, in a state where the suction button unit 61 is not pushed, the rubber spring 62 pushes up the pushing portion 61*b* toward an upper side in the penetrating direction C in FIG. 3 thus pressing the sealing portion 61*t* to the opening end 83*a*. Accordingly, a sealing state of the opening end 83*a* is maintained.

As shown in FIG. 5, in a state where the suction button unit 61 is pushed, the rubber spring 62 is compressed by the pushing portion 61*b* in the penetrating direction C. As a result, the suction leak holes 62*r* which communicate with the through hole 62*h* are closed.

With such a configuration, on one hand, as shown in FIG. 4, in a state where the suction button unit 61 is not pushed, the opening end 83*a* is closed by the sealing portion 61*t* and hence, the flow passage 90*i* and the flow passage 83*i* do not communicate with each other.

Accordingly, when the suction device 33 is driven, a gas A in the external space flows into the flow passage 83*i* through the suction leak holes 62*r* of the rubber spring 62 and the through hole 62*h*, and is suctioned by the suction device 33.

On the other hand, as shown in FIG. 5, in a state where the suction button unit 61 is pushed, the suction leak holes 62*r* are closed by the pushing portion 61*b* and the sealing portion 61*t* opens the opening end 83*a*.

Accordingly, the flow passage 90*i* communicates with the flow passage 83*i* and hence, when the suction device 33 is driven, a fluid E in a subject is suctioned from the opening 90a through the flow passage 90i, the flow passage 83i, the suction pipe sleeve 23 and the suction tube 43.

The gas feeding button unit 70 is mainly constituted of: the gas feeding button 71 which is an operation button; and a deforming portion 72 constituted of an elastic member.

As shown in FIG. 2 and FIG. 4, the gas feeding button 71 is disposed such that the gas feeding button 71 is inserted into the side hole 82h, and is disposed to be operable by pushing in the penetrating direction C of the side hole 82h.

An outer diameter of the gas feeding button 71 is formed smaller than an inner diameter of the side hole 82h. Accordingly, in a state where the gas feeding button 71 is not pushed, a region of the side hole 82h which is a portion into which the gas feeding button 71 is not inserted constitutes a passage through which the gas A in the flow passage 82i flows out to the external space.

As shown in FIG. 3 and FIG. 4, the deforming portion 72 is continuously connected with the gas feeding button 71, and is disposed in the gas feeding conduit 82.

As shown in FIG. 4, in a state where the gas feeding button 71 is not pushed, the deforming portion 72 is brought into contact with the inside of the gas feeding conduit 82 thus closing the flow passage 82i. As shown in FIG. 6, in a state where the gas feeding button 71 is pushed, the deforming portion 72 is deformed in the penetrating direction C thus opening the flow passage 82i.

More specifically, as shown in FIG. 3, FIG. 4 and FIG. 6, the deforming portion 72 is formed on a tubular member 73 on a downstream side with respect to the gas feeding button 71 as indicated by a chained line which surrounds the deforming portion 72. The tubular member 73 has a predetermined wall thickness, and an upstream side of the tubular member 73 is closed and a downstream side of the tubular member 73 is open.

FIG. 4 and FIG. 6 show a case where the gas feeding button 71 is integrally formed with the tubular member 73. However, the gas feeding button 71 may be constituted as a separate body from the tubular member 73. FIG. 4 and FIG. 6 show a case where the deforming portion 72 is integrally formed with the tubular member 73. However, the deforming portion 72 may be constituted as a separate body from the tubular member 73.

As shown in FIG. 4, on an outer periphery of the tubular member 73 on a downstream side, a closing portion 72e which is brought into contact with an inner wall 82n of the gas feeding conduit 82 in a state where the gas feeding button 71 is not pushed is formed in a circumferential manner.

As the closing portion 72e, for example, an O-shaped ring is named. As shown in FIG. 3, on the outer periphery of the tubular member 73 on an upstream side, a closing portion 73d such as an O-shaped ring may be mounted so as to be brought into contact with the inner wall 82n.

With such a configuration, in a state where the gas feeding button 71 is not pushed as shown in FIG. 4, a gas A which flows into the flow passage 82i from the gas feeding device 32 through the gas feeding tube 42 and the gas feeding pipe sleeve 22 cannot enter a downstream side with respect to the closing portion 72e in the flow passage 82i, that is, cannot enter the flow passage 90i by the closing portion 72e, and flows out to the external space from the side hole 82h.

The tubular member 73 is configured of the deforming portion 72 on the downstream side by forming a shape in which the downstream side is open as described above. Accordingly, as shown in FIG. 6, in a state where the gas feeding button 71 is pushed in the penetrating direction C, the tubular member 73 is deformed such that a volume of an inner space 73i on the downstream side decreases.

With such a configuration, as shown in FIG. 6, contacting of the closing portion 72e with the inner wall 82n is partially released, and the side hole 82h is closed by a finger F which pushes the gas feeding button 71 in the penetrating direction C.

Accordingly, a gas A which flows into the flow passage 82i from the gas feeding device 32 through the gas feeding tube 42 and the gas feeding pipe sleeve 22 advances toward the downstream side with respect to the closing portion 72e in the flow passage 82i, and enters the flow passage 90i.

As described previously, in a state where the gas feeding button 71 is not pushed as shown in FIG. 4, the closing portion 72e is brought into contact with the inner wall 82n thus closing the flow passage 82i. In such a state, not only a liquid R but also a gas is supplied to the flow passage 90i from the syringe 120 and hence, there is a case where a pressure on a downstream side with respect to the gas feeding button unit 70 changes intermittently to a negative pressure and a positive pressure with respect to an atmospheric pressure.

On one hand, in this case, when the pressure on the downstream side with respect to the gas feeding button unit 70 is a positive pressure, as shown in FIG. 4, the closing portion 72e comes to expand with respect to the inner wall 82n in a diameter increasing direction C1 in the penetrating direction C and hence, a contact force of the closing portion 72e to the inner wall 82n is increased. Accordingly, the gas feeding button unit 70 can close the flow passage 82i more strongly.

On the other hand, when the pressure on the downstream side with respect to the gas feeding button unit 70 is a negative pressure, as shown in FIG. 4, the closing portion 72e surely comes to contract in a diameter decreasing direction C2 so that the closing portion 72e is separated from the inner wall 82n in the penetrating direction C. However, the deforming portion 72 of the tubular member 73 has a predetermined wall thickness, and the closing portions 72e, 73d are brought into contact with the inner wall 82n and hence, the deforming portion 72 resists against a force in the diameter decreasing direction C2. Accordingly, the respective closing portions 72e, 73d are not separated from the inner wall 82n and hence, there is no possibility that the closure of the flow passage 82i is released.

Accordingly, in a state where the gas feeding button 71 is not pushed as shown in FIG. 4, there is no possibility that a liquid R flows backward toward an upstream side with respect to the gas feeding button unit 70 in the flow passage 82i of the gas feeding conduit 82. In other word, only in a state where the gas feeding button 71 is pushed as shown in FIG. 6, the upstream side and the downstream side with respect to the gas feeding button unit 70 in the flow passage 82i communicate with each other.

As described previously, with respect to FIG. 5, in a state where the suction button unit 61 is pushed, when a fluid E is suctioned from the flow passage 90i to the flow passage 83i, there is no possibility that a gas A flows into the flow passage 90i from the flow passage 82i and hence, lowering of a suction force can be prevented.

Other configurations of the gas feeding/suction valve 20 are equal to corresponding configurations in prior art and hence, the description of such other configurations is omitted.

In this manner, according to the embodiment, in the gas feeding conduit 82 connected to the endoscope conduit 90, the gas feeding button unit 70 is disposed in the intermediate portion of the flow passage 82*i* which communicates with the flow passage 90*i*.

The gas feeding button unit 70 is disposed in the intermediate portion of the gas feeding conduit 82, and has: the gas feeding button 71 which is inserted into the side hole 82*h* causing the flow passage 82*i* and the external space to communicate with each other, and is operable by pushing; the tubular member 73 on which the deforming portion 72 is formed.

The deforming portion 72 is formed on the tubular member 73 on the downstream side with respect to the gas feeding button 71, wherein the upstream side of the tubular member 73 is closed and the downstream side of the tubular member 73 is open. The deforming portion 72 includes the closing portion 72*e* formed on the outer periphery of the tubular member 73 on the downstream side with respect to the gas feeding button 71 such that the closing portion 72*e* is brought into contact with the inner wall 82*n* thus closing the flow passage 82*i* in a state where the gas feeding button 71 is not pushed.

The deforming portion 72 is deformed such that a portion of the closing portion 72*e* is separated from the inner wall 82*n* by a pushing operation of the gas feeding button 71 thus opening the flow passage 82*i*.

The deforming portion 72 of the tubular member 73 has a predetermined wall thickness.

With such a configuration, with the use of only a simple one member, that is, the gas feeding button unit 70 which is constituted of the gas feeding button 71 and the tubular member 73 including the deforming portion 72, it is possible to realize the flow passage 82*i* having the configuration where, in a state where the gas feeding button 71 is not pushed, the closing portion 72*e* is brought into contact with the inner wall 82*n* thus preventing opening of the flow passage 82*i*.

By deforming the deforming portion 72 only in the case where the gas feeding button 71 is operated by pushing, it is possible to realize the configuration where a portion of the closing portion 72*e* is separated from the inner wall 82*n* thus opening the flow passage 82*i*.

In a state where the gas feeding button 71 is not pushed, the closing portion 72*e* is brought into contact with the inner wall 82*n* thus closing the flow passage 82*i*. In such a state, even when a pressure on the downstream side with respect to the gas feeding button unit 70 changes intermittently to a positive pressure and a negative pressure, by the deforming portion 72 having a predetermined wall thickness, there is no possibility that contacting of the closing portion 72*e* with the inner wall 82*n* is released.

As described above, it is possible to provide the gas feeding/suction valve 20 and the endoscope 1 which include the configuration capable of preventing with certainty a backward flow of a liquid R toward an upstream side of the gas feeding conduit 82 which communicates with the endoscope conduit 90 simply and with a small number of parts.

In the above-mentioned embodiment, the gas feeding/suction valve 20 is described by exemplifying the case where the gas feeding conduit 82 and the suction conduit 83 are connected to the endoscope conduit 90, and feeding of a gas A from the flow passage 82*i* to the flow passage 90*i* and suction of a fluid E using the flow passage 83*i* from the flow passage 90*i* are switched.

The present invention is not limited to such a case, and it goes without saying that the embodiment is also applicable to the configuration where only the gas feeding conduit 82 is connected to the endoscope conduit 90, and the gas A is fed from the flow passage 82*i* to the flow passage 90*i*.

The present invention is not limited to the above-mentioned embodiment, and can be suitably modified without departing from the gist or the technical concept of the present invention read from claims, the entire specification and drawings.

What is claimed is:

1. A fluid control device for use with an endoscope, the fluid control device comprising:
    a gas feeding conduit having a flow passage through which a gas flows from an upstream side to a downstream side, the gas feeding conduit having a side hole;
    an operation button inserted into the side hole and disposed to be operable by pushing in a penetrating direction of the side hole; and
    a sealing surface connected with the operation button and disposed in the gas feeding conduit, the sealing surface configured to be brought into contact with an inside of the gas feeding conduit thus closing the flow passage in a state where the operation button is not pushed, and the sealing surface configured to be deformed in a penetrating direction thus opening the flow passage in a state where the operation button is pushed, wherein
    the sealing surface is disposed on the downstream side with respect to the operation button, the sealing surface having a closing portion contacting with an inner wall of the gas feeding conduit in the state where the operation button is not pushed, and
    the closing portion is provided only on the downstream side.

2. The fluid control device for endoscope according to claim 1, wherein the sealing surface is formed on a tubular member where an upstream side of the tubular member is closed and a downstream side of the tubular member is open, the closing portion is formed on an outer periphery of the tubular member on a downstream side, and
    the tubular member is configured to be deformed such that a volume of an inner space on the downstream side of the tubular member decreases in the state where the operation button is pushed.

3. The fluid control device for endoscope according to claim 1, further comprising a connecting portion connecting respective open ends of the gas feeding conduit on a downstream side and a suction conduit which is provided independently from the gas feeding conduit with an opening of an endoscope conduit on an upstream side that communicates with an inside of a subject such that the gas feeding conduit and the suction conduit communicate with the endoscope conduit.

4. The fluid control device for endoscope according to claim 3, further comprising a liquid feeding port configured to feed a liquid to the inside of the subject through the endoscope conduit, the liquid feeding portion being disposed on a downstream side with respect to the connecting portion in the endoscope conduit.

5. The fluid control device for endoscope according to claim 1, wherein a space between an inner surface of the side hole and an outer surface of the operation button comprises a passage through which the gas in the flow passage flows out to the external space in the state where the operation button is not pushed.

6. The fluid control device according to claim 1, wherein an entirety of an outer circumferential surface of the sealing surface maintains contact with the inner wall of the gas feeding conduit in a first state in which the flow passage is closed and a portion of the outer circumferential surface less than the entirety releases contact with the inner wall of the gas feeding conduit in a second state in which the flow passage is open.

7. The fluid control device for endoscope according to claim 1, wherein the operation button being movable within the side hole between a closed position sealing the flow passage at the downstream side of the gas feeding conduit and an open position opening the downstream side such that the gas flows through the flow passage, wherein in the closed position, the upstream side of the flow passage and an external space communicate with each other through the side hole allowing gas from the upstream side to flow to the external space.

8. An endoscope comprising:
   an insertion section in which a fluid conduit is disposed;
   an operation section continuously connected to the insertion section; and
   a fluid control device mounted on the operation section and having a conduit opening configured to communicate with the fluid conduit disposed in the insertion section, wherein
   the fluid control device comprises:
      a connecting portion disposed at a position different from the conduit opening and connected to a fluid source;
      a gas feeding conduit having a flow passage through which a gas flows from an upstream side which is a side of the fluid source to a downstream side which is a side of the conduit opening, the gas feeding conduit having a side hole;
      an operation button inserted into the side hole and disposed to be operable by pushing in a penetrating direction of the side hole; and
      a sealing surface connected with the operation button and disposed in the gas feeding conduit, the sealing surface configured to be brought into contact with an inside of the gas feeding conduit thus closing the flow passage in a state where the operation button is not pushed, and the sealing surface configured to be deformed in the penetrating direction thus opening the flow passage in a state where the operation button is pushed, wherein
   the sealing surface is disposed on a downstream side with respect to the operation button, the sealing surface having a closing portion contacting with an inner wall of the gas feeding conduit in the state where the operation button is not pushed; and
   the closing portion is provided only on the downstream side.

9. A fluid control device for use with an endoscope, the fluid control device comprising:
   a gas feeding conduit having a flow passage, the flow passage having an inner circumferential surface; and
   a sealing surface disposed in the gas feeding conduit, the sealing surface being configured to switch between a first state and a second state, the sealing surface having an outer circumferential surface, an entirety of which maintains contact with the inner circumferential surface in the first state and a first portion of the outer circumferential surface less than the entirety of the outer circumferential surface releases contact with the inner circumferential surface in the second state,
   wherein the sealing surface is provided only on a downstream side.

10. The fluid control device for endoscope according to claim 9, wherein the flow passage is closed in the first state and the flow passage is open in the second state.

11. The fluid control device for endoscope according to claim 9, further comprising an operation button inserted into a side hole of the gas feeding conduit, the operation button being movable in a penetrating direction of the side hole such that the operation button switches the sealing surface between the first state and the second state.

12. The fluid control device for endoscope according to claim 11, wherein a space between an inner surface of the side hole and an outer surface of the operation button comprises a passage through which gas in the flow passage flows out to an external space in the state where the operation button is not pushed.

13. The fluid control device for endoscope according to claim 11, wherein the operation button being movable within the side hole between a closed position sealing the flow passage at the downstream side of the gas feeding conduit and an open position opening a downstream side such that gas flows through the flow passage, wherein in the closed position, the upstream side of the flow passage and an external space communicate with each other through the side hole allowing the gas from the upstream side to flow to the external space.

14. The fluid control device for endoscope according to claim 9, wherein the sealing surface has a tubular shape having the first portion configured to deform in a radial direction of the gas feeding conduit.

15. The fluid control device for endoscope according to claim 14, wherein:
   the tubular shape comprises a first tubular portion and a second tubular portion, and
   the first tubular portion has the outer circumferential surface.

16. The fluid control device for endoscope according to claim 15, wherein the first tubular portion is provided proximally relative to the second tubular portion.

17. The fluid control device for endoscope according to claim 9, further comprising:
   a connecting portion connecting the gas feeding conduit and an endoscope conduit to communicate with each other, and
   a liquid feeding port provided distally relative to the gas feeding conduit, the liquid feeding port being configured to feed a liquid into the endoscope conduit.

18. The fluid control device for endoscope according to claim 17, further comprising,
   a suction conduit connected to the connecting portion and separately provided from the gas feeding conduit, and the suction conduit having a suction flow passage, and
   a suction operation button configured to be switched between a first position and a second position,
   wherein in the first position, the suction conduit is configured to communicate with the connecting portion, and to suction fluid from the connecting portion, and the sealing surface is in the first state, and
   wherein in the second position, the suction conduit is configured not to communicate with the connecting portion, and not to suction fluid from connecting portion, and the sealing surface is in the first state.

19. The fluid control device for endoscope according to claim 9, wherein the sealing surface is formed on a tubular member where an upstream side of the tubular member is closed relative to the inner circumferential surface of the gas feeding conduit and a downstream side of the tubular member is open relative to the inner circumferential surface of the gas feeding conduit.

20. An endoscope comprising:
   an insertion section;

an operation section continuously connected to the insertion section; and the fluid control device for endoscope according to claim 9 disposed in the operation section.

* * * * *